United States Patent [19]

Holmes

[11] 4,361,110

[45] Nov. 30, 1982

[54] APPARATUS FOR MONITORING AND CONTROLLING THE DISTRIBUTION OF DROPLETS ON A SURFACE

[75] Inventor: James F. Holmes, Portland, Oreg.

[73] Assignee: Oregon Graduate Center for Study and Research, Beaverton, Oreg.

[21] Appl. No.: 200,891

[22] Filed: Oct. 27, 1980

[51] Int. Cl.³ .................... B05B 12/08; C01B 11/28
[52] U.S. Cl. .................................. 118/665; 356/445
[58] Field of Search ...................... 118/665; 356/445

[56] References Cited

U.S. PATENT DOCUMENTS 3,185,024  5/1965  McCreanor .................... 118/665
3,819,948  6/1974  Iijima et al. ................. 118/665 X

*Primary Examiner*—James R. Hoffman

*Attorney, Agent, or Firm*—Kolisch, Hartwell & Dickinson

[57] ABSTRACT

Apparatus for monitoring the weight of glue sprayed on a veneer surface, where the light reflectance from droplet-covered regions on the surface differs from that of uncovered surface regions. A beam of light is directed onto the sprayed surface of a relatively moving veneer, and the light reflectance from a zone within the illuminated surface area is detected to produce a signal which varies according to instantaneously detected reflected light level. A signal-handling circuit in the apparatus transforms the signal to a binary data stream composed of one and other data states representing reflected light levels from droplet-covered and uncovered regions on the surface, respectively. The data stream is processed to compute the weight of glue sprayed on the surface.

10 Claims, 5 Drawing Figures

D 000000000000111100000000000011100000011000011111110000

APPARATUS FOR MONITORING AND CONTROLLING THE DISTRIBUTION OF DROPLETS ON A SURFACE

BACKGROUND AND SUMMARY

The present invention relates to surface monitoring, and in particular, to apparatus for monitoring certain distribution characteristics of droplets distributed over a surface. For the purpose of explanation, a preferred embodiment of the invention is described herein in conjunction with the manufacture of plywood where it has been found to have particular utility.

It is desirable, in the manufacture of ply articles such as plywood, to monitor and control the weight of glue sprayed onto the individual ply or veneer. One approach which may be used to monitor applied glue-weight is to determine the size and density distribution characteristics of the droplets on the veneer, where these characteristics are related in a known way to the weight of glue applied. It is advantageous, in such monitoring, to be able to distinguish and reject from the glue-weight calculation, surface features such as holes, knots and gaps between adjacent veneer pieces.

A variety of devices used to monitor surface characteristics in traveling workpieces are known in the prior art. Typically in such devices, the angle of light reflected from the surface of a moving workpiece is determined to provide a measure of surface roughness or other irregularities. Devices such as these are generally ineffective in monitoring droplet-like surface features which tend to have relatively flat surfaces and therefore reflect light at an angle which is indistinguishable from that of uncovered surface regions.

Accordingly, one general object of the present invention is to provide apparatus for monitoring the size and density distribution of glue droplets or the like applied to a traveling workpiece.

Another object of the invention is to provide such an apparatus which is capable of distinguishing droplets on a workpiece surface from relatively large features such as surface holes, knots and gaps between adjacent workpieces.

Still another object of the invention is to provide such an apparatus which is capable of monitoring the performance of a glue applicator, and of controlling the glue application rate thereof.

The apparatus of the present invention includes a light source for directing a beam of light onto the surface of a traveling workpiece, where the surface of the workpiece has been sprayed with droplets whose light reflectance differs in a known way from that of uncovered regions of the surface. The level of light reflected from the traveling surface is detected by a photodetector which produces a signal that varies according to the instantaneously detected reflected light level. The signal is transformed to a related binary data stream composed of one and other voltage states representing reflected light levels from covered and uncovered regions, respectively, on the surface. Droplet distribution characteristics related to the weight of glue applied to the workpiece surface are computed from the data stream.

In a preferred embodiment of the invention, the apparatus of the invention includes a bit gate filter for ignoring, in the data stream, sequences having a predetermined number of successive, identical data states. This filter enables the apparatus to distinguish droplets from large non-droplet surface features such as those mentioned above.

BRIEF DESCRIPTION OF THE DRAWING

These and other objects and features of the present invention will become more fully apparent when the following detailed description of the invention is read in connection with the accompanying drawings, wherein.

DETAILED DESCRIPTION OF THE INVENTION

Figure 1:
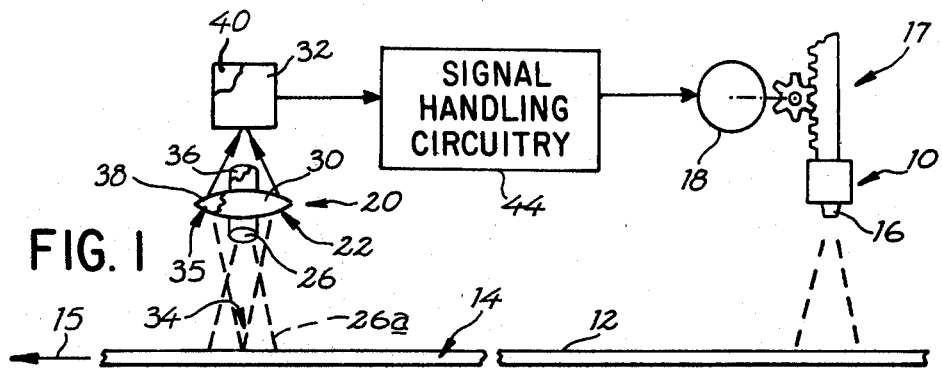
FIG. 1 is a simplified view of apparatus constructed according to the present invention, shown in an intended setting.

The setting in which the present invention is intended to operate is shown in FIG. 1. The figure illustrates in simplified form a conventional spray device 10 which operates to spray a liquid onto the upper surface 12 of a workpiece 14 traveling below the spray device in a right-to-left direction in the figure as indicated by arrow 15. In the particular setting shown and described herein, workpiece 14 is a ply, or veneer, used in forming a plywood sheet, such veneer having typical planar dimensions of four feet by eight feet. The workpiece is moved by a conveyor or the like (not shown), with typical travel speeds ranging from about 50 to 100-feet-per-minute.

Figure 3:
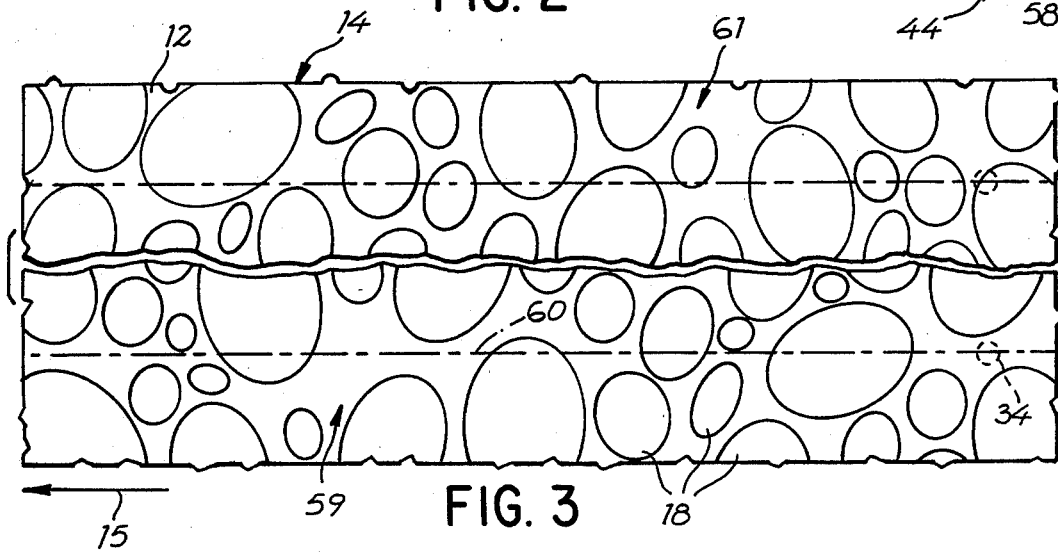
FIG. 3 is an enlarged plane view of a portion of a sprayed workpiece surface.

Device 10 includes an air-driven spray nozzle 16 which produces and dispenses a liquid glue spray. The nozzle is constructed to apply the glue spray to a substantially rectangular area on the upper surface of the workpiece extending across the width thereof. There are thus distributed on the upper surface of the workpiece spray droplets, such as droplets 18 seen in FIG. 3. In a typical glue-spray device used to apply glue droplets to plywood veneer, the droplets range in size from about 0.025-inches to 0.35-inches. The smallest droplets seen in FIG. 3 are representative of droplets in the lower size range.

According to an important requirement in the operation of the present invention, the light reflectance from the spray droplets differs in a known way from light reflectance from workpiece surface regions not covered by droplets. Specifically, the glue droplets have a lower light reflectance than uncovered regions of the surface, and thus appear as relatively dark spots on a relatively light surface background.

The amount of glue applied to workpiece 14 can be controlled typically either by varying workpiece travel speed, or by adjusting the height of the spray head above a workpiece. The latter approach is preferred and can be accomplished by suitable gearing, such as the rack and pinion gearing shown at 17 in FIG. 1, with a drive motor, indicated schematically at 18 in FIG. 1, drivingly connected to the pinion in gearing 17. Device 10 is preferably adjusted to produce an applied glue weight which typically is in the range of about 35 to 45-pounds-per-1,000 square feet of veneer.

Apparatus constructed according to the invention is shown at 20 in FIG. 1. An examining module 22 in the apparatus includes a light source 26 for directing a beam 26a of light onto a region on the workpiece surface being monitored. Source 26 is preferably a light-emitting diode which emits infrared light.

Focusing means in module 22, represented in FIG. 1 by a lens 30, is used to focus light from a defined small viewing zone 34 within the just-mentioned illuminated region to a photodetector 32 located above the lens. Zone 34 is shown in FIG. 3 by a dashed-line circle. Zone 34 is preferably somewhat smaller than the smallest droplets on the workpiece, and herein has a diameter of about 0.02-inches. Photodetector 32 responds to the level of light received from zone 34 and outputs an analog signal proportional to the instantaneously detected light level reflected from the zone. If glue is being observed (dark) the output signal is larger than if the uncovered surface is being observed.

Apparatus 20 herein includes additional examining modules, such as module 35 shown in FIG. 1 behind module 22. The light source, lens and photodetector in module 35 are indicated at 36, 38, 40, respectively, in this figure. Where a workpiece having a four-foot width is to be monitored, it is contemplated that eight such examining modules, substantially equally laterally spaced across the width of the workpiece, be used.

Figure 2:
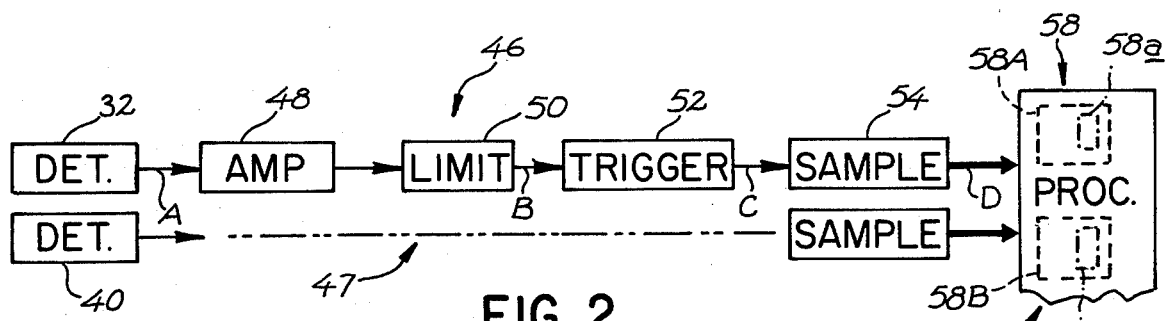
FIG. 2 (second sheet of drawings) is a block diagram showing signal-handling circuitry used in the invention.

Analog signals produced by the photodetectors in the apparatus are fed to signal-handling circuitry shown at 44 in FIG. 1. With reference to FIG. 2, circuitry 44 includes, for each photodetector, transforming means comprising a signal-processing unit, such as unit 46 associated with photodetector 32, and an identical unit 47 illustrated in part by a dash-dot line in FIG. 2, associated with photodetector 40. Unit 46, which is representative, includes an amplifier 48 followed by a signal limiter 50, a trigger 52, and a signal sampler 54. Limiter 50 clips the amplified signal from amplifier 48, and trigger 52 responds to the positive-voltage portions of the clipped signal to generate related positive-going signal waves which define different-length "one" and "zero" binary states. A "one," or high, state corresponds to observance of a droplet, and a "zero," or low, state corresponds to observance of the uncovered surface. Sampler 54, which operates at a preferred sampling frequency of about 500-Hz, responds to the output signal from trigger 52 to convert the same into a higher frequency, repetitive stream of corresponding "zero" and "one" states referred to herein as a binary data stream. The construction of each of the different elements in signal-processing unit 46 is conventional in the art.

The binary data stream produced by each of the signal-processing units in the apparatus is inputted a microprocessor associated with each examining module and forming part of a processor 58 shown in FIG. 2. As indicated here, data from units 46, 47 is fed to microprocessors 58A, 58B, respectively, in processor 58. Each of the micro-processors in processor 58 acts on its inputted binary data stream to compute applied glue weight, and other characteristics, related to the distribution of glue droplets on the workpiece.

Each micro-processor is equipped with what is referred to herein as a bit gate filter to remove from the data stream unwanted data sequences having a predetermined number of successive identical data states. These, herein, are the sequences which reflect the observance of non-droplet larger surface features. Microprocessor 58A includes a bit gate filter 58a, and microprocessor 58B includes a similar filter 58b. These filters have a construction which will become apparent to those skilled in the art with regard to the discussion below concerning the flow diagram of FIG. 5.

Where, as here, apparatus 20 is constructed to monitor the workpiece at several laterally spaced regions, such as regions 59, 61 in FIG. 3, processor 58 further includes a central micro-processor (not shown) used in comparing and averaging droplet distribution characteristics computed by the individual micro-processors associated with each of the examining modules in the apparatus. The central micro-processor is also designed to output an appropriate signal for controlling the operation of motor 18, to regulate the density of spray being applied to the workpiece. Processor 58 and motor 18 (FIG. 1), which are also referred to herein as computing means and connecting means, respectively, thus provide means for regulating the distributed output of device 10 according to the characteristics computed by the processor. The design of processor 58, like the designs of the individual elements in above-described signal-processing units, is well known to one skilled in the art.

Figure 4:
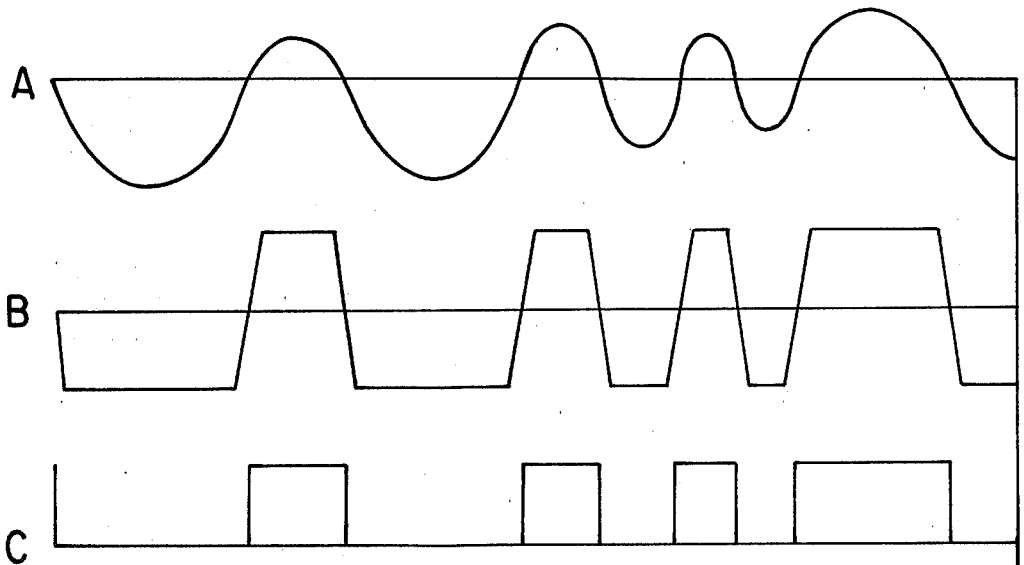
FIG. 4 illustrates, at A, a light-level signal produced by the present invention and related to the droplet distribution of a portion of the surface shown in FIG. 3, and at B and C, successive signals produced by the apparatus in transforming signal A to a data stream, represented at D in the figure.

Considering operation of apparatus 20, a sprayed workpiece surface, portions of which are shown in FIG. 3, travels at a known rate beneath the examining modules in the apparatus. A beam of light, such as beam 26a, is directed from each examining module onto the traveling workpiece, and the level of light reflectance from each illuminated defined zone, such as zone 34 in FIG. 3, is detected by the associated photodetector, such as detector 32. The photodetector converts the light level detected into an analog signal which is proportional to the darkness of the area observed. In FIG. 4, signal A represents a detector-produced analog signal corresponding to the monitored portion of the workpiece in FIG. 3 extending along dash-dot line 60 in this figure. Signal A is represented on a time scale which permits a direct comparison between the workpiece surface features observed by the detector and the signal produced thereby. As can be seen, signal regions above and below a reference base line in signal A correspond to droplet-covered and uncovered surface regions, respectively.

Signal A, when amplified by amplifier 48 and clipped by limiter 50, assumes the signal shape shown at B in FIG. 4. Trigger 52 generates, in response to the signal from limiter 50, square wave pulses which create the "zero" and "one" states mentioned earlier. A trigger output signal corresponding to signal B is seen at C in FIG. 4. The trigger output is converted by sampler 54 to a binary data stream, represented by a string of Arabic numerals at D in FIG. 4, reflecting "one" and "zero" data states which correspond to relatively low and relatively high monitored levels of light reflectance, respectively. It is noted here that at a board travel speed of about 60-feet-per-minute, and a sampling rate of about 500-Hz, sampler 54 generates about five hundred data states per foot of monitored workpiece.

Figure 5:
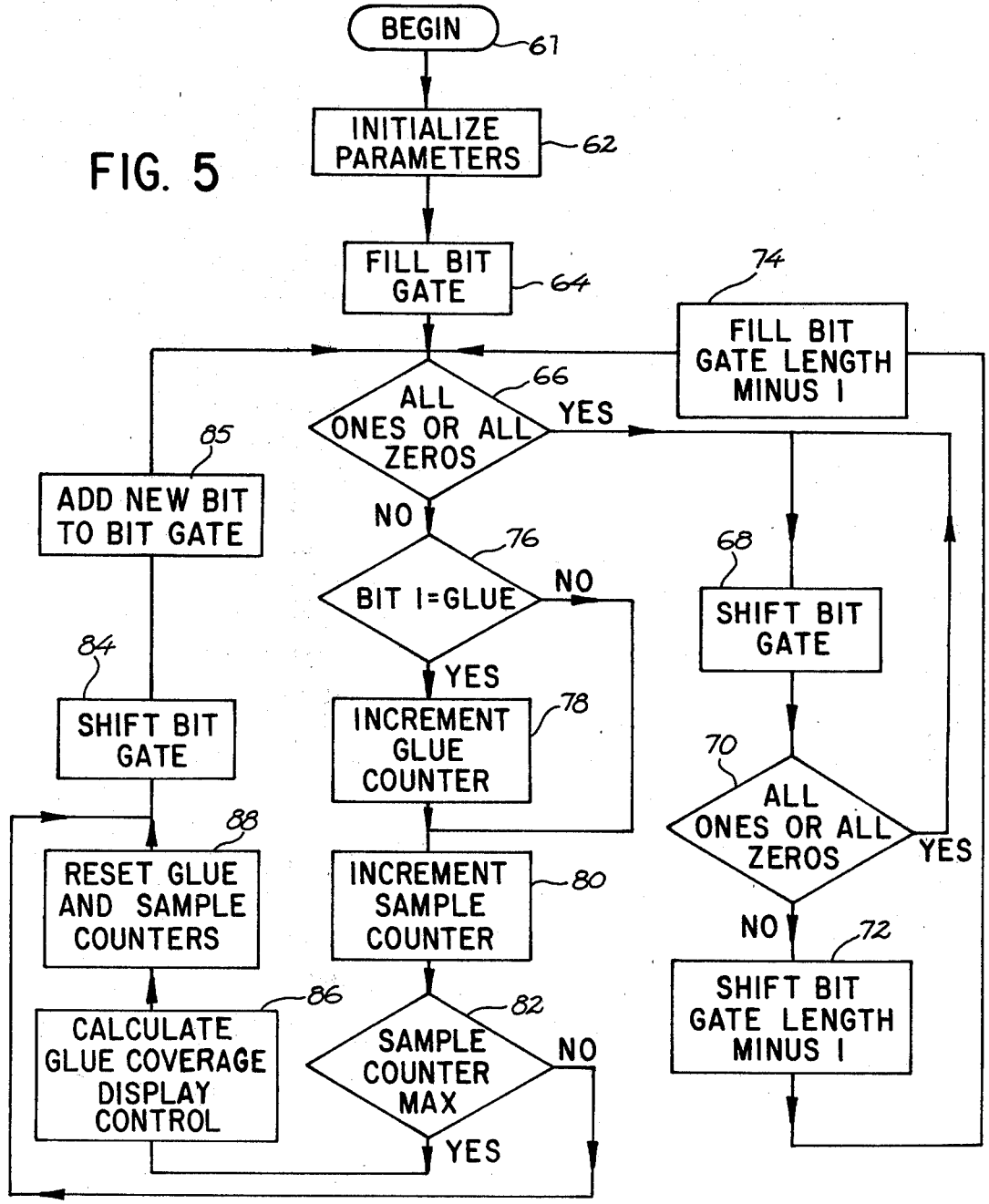
FIG. 5 is a schematic flow diagram of the algorithm used in processing data in the present invention.

The algorithm represented by the flow diagram in FIG. 5 illustrates how each bit gate filter in the present invention operates to eliminate data stream sequences characterized by the same data state and having a number of data bits exceeding a preselected number of bits.

Also illustrated in FIG. 5 are the algorithm steps for calculating, ultimately, glue coverage information.

Describing the operation of the apparatus with reference to FIG. 5, this operation will be explained in terms of each block in the diagram performing a certain function. Thus, an appropriate start signal is generated by block 61 followed by performance of block 62 to initialize all parameters in the system and to clear all data-storage registers. With system initialization complete, control is taken over by block 64 which fills the associated bit gate (register) with a predetermined number of the next successively arriving data bits derived from viewing the traveling veneer sheet. In the present apparatus, a register size capable of holding 16-data bits has been selected and has proved to be entirely satisfactory. Thus, the first 16-data bits next to arrive are loaded serially in the appropriate register, and are then tested under the control of block 66 to determine whether these bits are all "ones" or "zeros". If this test is positive, and determines that there are indeed all "ones" or "zeros" in the register, such a condition indicates current viewing of a surface feature, as mentioned earlier, which is larger than the expected sizes of glue droplets, and which must be ignored. Accordingly, control branches from block 66 to block 68. Under control of the latter mentioned block, the contents of the bit gate are shifted by one bit, with the result that the earliest received bit is discarded, the next received 15-bits are retained, and the next new bit is entered. With this operation complete, the condition of the gate is tested under the control of block 70 which performs in substantially the same manner as previously mentioned block 66. If the test performed by block 70 determines that the gate houses all "ones" or "zeros" control branches from the right in FIG. 5 from block 70 into a subloop with block 68 which performs again as previously described. This subloop will continue until block 70 determines that the bit gate no longer contains all "ones" or "zeros." When this situation is found, control shifts to block 72.

What than happens is that block 72 shifts out of the gate all but the last received bit, and turns over control to block 74. Block 74 performs to fill the remaining 15-spaces in the gate with the next 15-received data bits, and on completing this returns control to test block 66. Block 66, of course, performs in the manner previously described.

If block 66 determines that the associated bit gate does not contain all "ones" or "zeros" control branches to block 76. This block tests the binary status of the first (oldest) bit in the register. Specifically, it tests to determine whether this bit is a "one," representing observed glue, or "zero," representing an observed nonglue surface area. If the determination is that the bit is a "one," control flows to block 78 which increments what is referred to herein as a glue counter. If it determines that the bit is a "zero," control bypasses block 78 as can be seen, and is transferred to block 80. Regardless of whether block 76 determines that there is or is not an observed glue area, control ultimately flows to block 80 which increments by a count of "one" what is referred to herein as a sample counter.

Experience with the apparatus of the invention has shown that a reasonable way of acquiring data preparatory to calculating glue coverage is to sample over about an 8-foot length of a sheet of veneer. With the travel speed and sampling rate mentioned earlier, this is accomplished by acquiring about 4,000 data samples.

Thus, from block 80 in the algorithm, control flows to block 82 which tests the count condition of the sample counter to determine whether the count in the counter is than at 4,000. If the count tested is lower than 4,000, control branches directly to block 84 which performs in substantially the same manner as previously mentioned block 68 and which transfers control through block 85 to block 66. Block 85 adds a new bit to the bit gate.

If, on the other hand, the tested sample counter reveals a full count of 4,000, control branches to block 86 which results in a glue coverage calculation being performed in accordance with the then count status of the glue counter and the sample counter. The result of this calculation is then used, if necessary, to effect an appropriate adjustment in the position of spray device 10.

Following performance by block 86, control is transferred to block 84 through a block 88 which resets the glue counter and the sample counter to "zero" count conditions.

From the foregoing, it can be appreciated how various objects of the invention are met. The apparatus can be adapted to monitor surface features in a traveling workpiece in a variety of settings where such features are characterized by differential light reflectance. The apparatus is readily adapted for use with a spray device or the like, to regulate the amount of material being sprayed onto a workpiece according to the droplet weight computed by the apparatus. Further, the apparatus can also be used to control and regulate the fraction or percentage of surface coverage by glue. By applying a selectable-length bit gate filter in the apparatus, surface features having a larger-than-desired size can be ignored in the glue weight computation performed. By using multiple filters having different bit gate lengths, the number of features encountered of a given size may be found and/or the glue drop size distribution may be determined.

Where a number of laterally spaced examining modules are employed in the apparatus, various averaging computations can be made to improve the accuracy of the glue weight determination performed. Further, by comparing the outputs of a number of such modules, technical problems such as line stoppage in the spray device, nonuniform spray application across the width of the workpiece, or malfunctioning in any one of the examining modules can be detected readily.

While a preferred embodiment of the invention has been described herein, it is apparent that various changes and modifications may be made without departing from the spirit of the invention.

It claimed and desired to secure by Letters Patent:

1. Apparatus for monitoring in a defined viewing zone certain area distribution characteristics of discrete droplets distributed as islands over a surface in a workpiece moving relative to the zone, where the light reflectance of the droplets differs in a known way from that of the surface, said apparatus in operative condition comprising a light source for directing a beam of light into said zone, a photodetector mounted adjacent said source for detecting the level of light reflected from said zone, and for producing a signal which varies according to the instantaneously detected reflected light levels, means connected to said photodetector to transform said signal to a related binary data stream composed of one and other data states representing reflected light levels from covered and uncovered regions, respectively, of the surface, and means connected to said transforming means to compute such characteristics from the data stream.

2. The apparatus of claim 1, wherein said computing means includes gate means for ignoring in said data stream data sequences having a predetermined number of successive identical data states.

3. The apparatus of claim 1 in which distributed droplets have area sizes within a known size range, and wherein the area of said zone is related in a known manner to the size of said range.

4. The apparatus of claim 1 in combination with a spray device operable to spray such droplets onto such surface, said apparatus further comprising means operatively connecting said computing means to said device to regulate the spray output of the latter according to said characteristics computed by the former.

5. In a system having a spray device for applying discrete liquid droplets as islands to the surface of a substantially planar workpiece which is moving in its plane with respect to the device, to produce a partial covering of such surface with droplets whose reflectance differs from that of uncovered regions on the surface, apparatus for controlling the percentage of area of the surface covered by such droplets comprising a light source mounted downstream of such device for directing a beam of light onto such workpiece in a defined viewing zone, a photodetector mounted adjacent said source for detecting the level of light reflected from said zone, and for producing, as the workpiece moves with respect to the zone, a signal which varies according to the instantaneously detected light level, means connected to said photodetector to transform said signal to a binary data stream composed of one and other data states representing reflected light levels from covered and uncovered regions, respectively, of the surface, and control means operatively connecting said transforming means and said spray device to regulate the spray output from the latter according to the data stream produced by the former.

6. The apparatus of claim 5, in which distributed droplets have area sizes within a known size range, and the area of said zone is related in a known manner to the size of said range.

7. The apparatus of claim 6, wherein the beam illuminates an area larger than that of said zone, and said photodetector includes focusing means defining the size of said zone.

8. The apparatus of claim 5, wherein said control means includes gate means for ignoring in said data stream data sequences having a predetermined number of successive indentical data states.

9. Apparatus for monitoring in each of a plurality of laterally distributed defined viewing zones certain area distribution characteristics of discrete droplets distributed as islands over a surface in a workpiece moving relative to the zones, where the light reflectance of the droplets differs in a known way from that of the surface, said apparatus, in operative condition, comprising for each zone, a light source for directing a beam of light into the zone, a photodetector mounted adjacent said source for detecting the level of light reflected from the zone, and for producing a signal which varies according to the instantaneously detected reflected light level, means connected to said photodetector to transform said signal to a related binary data stream composed of one and other data states representing reflected light levels from covered and uncovered regions, respectively, of the surface, and means operatively connected to said transforming means for computing such characteristics from the data stream.

10. The apparatus of claim 9, wherein said computing means comprises part of a data processor which is constructed further to monitor the lateral uniformity of droplet distributions in the different zones.

* * * * *